United States Patent [19]

Palepu

[11] Patent Number: 5,268,368
[45] Date of Patent: Dec. 7, 1993

[54] CYCLOPHOSPHAMIDE—AMINO ACID LYOPHILIZATES

[75] Inventor: Nageswara R. Palepu, Dublin, Ohio
[73] Assignee: Erbamont, Inc., Dublin, Ohio
[21] Appl. No.: 703,470
[22] Filed: May 17, 1991
[51] Int. Cl.$^5$ ............................................. A61K 31/66
[52] U.S. Cl. .................................. 514/110; 514/960; 562/575
[58] Field of Search ............... 514/110, 960; 562/567, 562/575

[56] References Cited

U.S. PATENT DOCUMENTS 4,537,883  8/1985  Alexander et al. ................. 514/110
5,066,647  11/1991  Palepu et al. ....................... 514/110

FOREIGN PATENT DOCUMENTS 0083439  7/1983  European Pat. Off. .
0271622  6/1988  European Pat. Off. .
2183913  12/1973  France .
2322605  4/1977  France .

OTHER PUBLICATIONS

Osswald, "Potentiated Chemotherapeutic Activity..." Arzneimihelforschung. 25(10):1608–09, Oct. 1975.
European search report, EP304223, (Mar. 1991).

Primary Examiner—Glennon H. Hollrah
Assistant Examiner—Brian M. Burn
Attorney, Agent, or Firm—Thompson, Hine and Flory

[57] ABSTRACT

A stable rapidly dissolving lyophilized composition of cyclophosphamide and an amino acid selected from the group consisting of glycine, valine and serine is provided which contains an amount of water which is equimolar to the amount of amino acid and the amount of cyclophosphamide in said composition; the composition is preferably prepared from a solution containing at least 2% (W/V) of the amino acid and having a pH in the range of 5.0 to 7.0.

8 Claims, No Drawings

1

CYCLOPHOSPHAMIDE—AMINO ACID LYOPHILIZATES

BACKGROUND OF THE INVENTION

1. Field of the Invention

The present invention relates to a novel lyophilized composition containing cyclophosphamide and a low molecular weight amino acid as an excipient.

2. Description of Prior Art

Cyclophosamide is a nitrogen mustard for use as a antineoplastic for treatment of malignant lymphomas, multiple myeloma, chronic and acute lukemias, mycosis fungoides, neuroblastoma, adenocarcoma of the ovary, retinoblastoma and carcinoma of the breast. Cyclophosamide is commercially available as a sterile powder for parenteral use when reconstituted with sterile water for injection, as a tablet for oral use or as a lyophilizate to be reconstituted with sterile water for injection.

U.S. Pat. No. 4,537,883 to Alexander et al. (Mead Johnson & Co.) discloses various lyophilizates of cyclophosphamide. These lyophilizates are prepared by lyophilizing a solution of cyclophosphamide and one or more excipients and hydrating the product such that it contains about 4% moisture. The patent is based upon a comparative study of lyophilizate cakes and the dissolution time for lyophilizates of cyclophosphamide prepared using a number of excipients. The study concludes that the lyophilizate prepared with mannitol gives a better cake and faster dissolution time than the lyophilizates prepared with other excipients. The patent also teaches that the lyophilized cyclophosphamide-mannitol composition exhibits better thermal stability if it contains an equimolar amount of water based on cyclophosphamide. The preferred lyophilizate contains 20 parts cyclophosphamide, 1.25 to 2 parts water and 10 to 85 parts mannitol. Among the excipients evaluated in the patent were mannitol, sodium bicarbonate, lactose, polyvinyl pyrrolidone (PVP), arginine, and tartaric acid and combinations of mannitol and various organic acids including the mino acids glycine and arginine as secondary excipients. The lyophilizates illustrated in the patent prepared with the amino acids provided poor cakes which exhibited poor dissolution times.

A study of "The Stability of Cyclophosphamide in Lyophilized Cakes" by Kovalcik and Guillory, J. Parenteral Science & Technology, Vol. 42, No. 1, pp. 29-37 (1988) discloses sodium bicarbonate lyophilizates prepared using a 1:4 weight ratio of cyclophosphamide to sodium bicarbonate with a 5% water content of total weight of the lyophilizate. The sample cakes showed a 5% loss in potency when left at room temperature for 53 days and 4% loss in potency when stored at room temperature for 117 days.

Practical problems have occurred preparing a composition having a 1:4 ratio of cyclophosphamide to sodium bicarbonate in that special large vial sizes are required to obtain a lyophilizate cake. In addition, the solids of such ratios are not readily soluble and hydration time is undesirably long due to high sodium bicarbonate concentration and the amount of water necessary is greater than the sum of the mole equivalent of cyclophosphamide and the mole equivalent sodium bicarbonate.

SUMMARY OF THE INVENTION

It has now been found that lyophilizates of cyclophosphamide having improved dissolution times and good shelf stability can be obtained using amino acids selected from the group consisting of valine, glycine and serine as the bulking agent. Lyophilizates in accordance with the present invention generally contain about 5 to 10 parts by weight water and about 50 to 150 parts by weight of the amino acid per 100 parts by weight cyclophosphamid. The amount of water in the lyophilizate is preferably about equimolar to the amount of cyclophosphamide. In addition to dissolving quickly, these lyophilizates generally experience less than 5% loss in potency when stored at 37° C. for a period of six weeks. This means that the compositions should be stable at room temperature for about 24 months.

Accordingly, one object of the present invention is to provide a lyophilizate of cyclophosphamide using the aforementioned amino acids as bulking agents which provides a good cake which dissolves rapidly when reconstituted with water and provides good shelf stability.

Another object of the present invention is to provide a lyophilizate wherein the lyophilizate contains water in an amount which is equimolar to the amount of cyclophosphamide to about 3% in excess thereof.

These and other objects are achieved in accordance with the present invention which is described below in more detail.

DETAILED DESCRIPTION OF THE INVENTION

Previously, as disclosed in U.S. Pat. No. 4,537,883, unsatisfactory lyophilizates have been obtained using the amino acids arginine and glycine as excipients. In particular, previous lyophilizates provided poor quality cakes which were slow to dissolve. Contrary to the teachings in the patent, it has now been found that lyophilizates of cyclophosphamide and the amino acids glycine, valine and serine can be obtained having good shelf life and minimum dissolution time.

The amino acids are preferably used in their neutral form as opposed to their salt form. The amino acids may be used as the DL racemate or as the D or L optical isomer.

Conventional lyophilization techniques can be used in the present invention include the methods described in U.S. Pat. No. 4,537,883, among other methods known to those skilled in the art. The conditions employed in the Example which follow are one example of those which can be used.

Following lypohilization, the lyophilizate is hydrated. Hydration can be accomplished by aspirating water into the vial containing the lyophilizate using an ultrasonic spray nozzle which delivers a predetermined amount of water or by placing the vial in a humidity chamber having a relative humidity exceeding 85%. In addition, hydration techniques may also be accomplished by the process disclosed in U.S. Pat. Nos. 4,659,699 and 4,537,883 which are incorporated herein by reference. One feature of the present invention is that the lophilizate is hydrated such that it contains an amount of water which is about equimolar to the amount of cyclophosphamide. While the compositions may be hydrated such that they contain water in excess of an equimolar amount, if the amount of water present in the lyophilizate exceeds an equimolar amount by more than 3%, the stability of the lyophilizate may diminish. If the lyophilizate contains less than an equimolar amount of water, a portion of the cyclophosphamide dosage may be present in the less stable amorphous and/or anhydrate form. By Karl Fisher analysis, the amount of water is about 5 to 10 parts by weight per 100 parts cyclophosphamide.

It has been observed that the concentration of the amino acid in the pre-lyophilized bulk solution may affect its shelf stability. The lyophilizates are preferably prepared by lyophilizing solutions containing about 1 to 3% amino acid and about 2 to 4% (W/V) cyclophosphamide. The pH of the solution may affect stability. It has been found that lyophilizates prepared from solutions containing at least 2% (W/V) amino acid and having a pH in the range of 4 to 8 and preferably 5 to 7 provide superior shelf stability. Higher concentrations of amino acid can be used but with little effect on stability; generally about 1 to 5% (W/V) bulk solutions are used.

Neutralization of the reconstituted solution is not necessary if the reconstituted solution is administered in large volumes of saline in which case the effect of the reconstituted solution on the pH of the solution administered to the patient is negligible.

In the preferred lyophilized compositions of the present inventions the amount of water is about equimolar to the amount by mole of weight of cyclophosphamide (about 2 to 6% based on the total weight of the lyophilizate as determined by the Karl-Fischer method), and the weight ratio of cyclophosphamide to amino acid is from about 2:1 to 2:3.

The effect of amino acid selection, the concentration of the pre-lyophilized solution, and the water content of the lyophilizate on the stability of cyclophosphamide lyophilizates is illustrated in the following non-limiting example.

EXAMPLE

Lyophilizates of cyclophosphamide and amino acids were prepared as follows:

Solutions (5 ml) containing 2% (W/V) cyclophosphamide (CP) and amino acids in the percentages indicated in the following table were placed in 10 cc vials. The vials were frozen in a lyophilization chamber for about 12 hours at a shelf temperature of −26° C. The chamber was then evacuated to a pressure of about 100 millitorr. The samples were maintained in the chamber at a shelf temperature of 0° C. for 16 hours and 25° C. for 8 hours. The samples were hydrated by placing them in an 85% humidity chamber and monitoring the weight gain. The amount of water in the lyophilizate expressed as a percent of the total composition and as a percentage of cyclophosphamide is shown in the table.

The samples were next subjected to an aging study wherein they were first assayed by HPLC, then placed in an oven at 37° C. for the periods indicated and finally re-assayed. The loss in potency expressed as a percentage loss based on the initial assay is shown in the table.

TABLE

| Sample No. | Bulking Agent | CP: Amino Acid Wt. Ratio % | % Water[1] | % Water-CP[2] | Age (wks.) | Loss in Potency (%) |
|---|---|---|---|---|---|---|
| 1 | Glycine | 2:1.5 | 4.8 | 8.5 | 18 | 2 |
| 2 | Glycine | 2:3 | 2.5 | 7.9 | 18 | 2 |
| 3 | Serine | 2:3 | 2.9 | 7.5 | 18 | 2-3 |
| 4 | Valine | 2:3 | 3.3 | 8.8 | 18 | 3-4 |
| 5 | Serine | 2:3 | 2.2 | 5.7 | 18 | 84 |

[1] percentage of total vial
[2] percentage based on cyclophosphamide

Having described the invention in detail and by reference to preferred embodiments thereof, it will be apparent that modifications and variations are possible without departing from the scope of the invention defined in the appended claims.

What is claimed is:

1. A lyophilized cyclophosphamide composition comprising cyclophosphamide, an amino acid selected from the group consisting of serine, glycine and valine, and water wherein based on 100 parts cyclophosphamide said water is present in an amount of about 5 to 10 parts by weight and said amino acid is present in an amount of about 50 to 150 parts by weight and the weight ratio of cyclophosphamide to amino acid is from about 2:1 to 2:3.

2. The composition of claim 1 wherein said water is present in said lyophilized composition in an amount of about 2 to 6 percent by weight based upon the total weight of said composition.

3. The composition of claim 1 wherein said composition is prepared from a solution of cyclophosphamide and amino acid in water having pH in the range of approximately 4 to 8.

4. The composition of claim 3 wherein said solution possesses a pH in the range of about 5.0 to 7.0.

5. The composition of claim 1 wherein said amino acid is selected from the group consisting of DL-glycine, DL-serine, DL-valine, L-Glycine, D-glycine, L-Valine, D-Valine, L-Serine and D-Serine.

6. The composition of claim 5 wherein said amino acid is DL, L, or D valine.

7. The composition of claim 5 wherein said amino acid is DL, L, or D serine.

8. The composition of claim 5 wherein said amino acid is DL, D or L glycine.

* * * * *